(12) United States Patent
Veltri et al.

(10) Patent No.: US 8,347,754 B1
(45) Date of Patent: Jan. 8, 2013

(54) MULTI ARTICULATING ROBATIC INSTRUMENT

(75) Inventors: Jeffrey Allan Veltri, Burlington (CA); Uwe Dirk Schaible, Ancaster (CA)

(73) Assignee: Titan Medical Inc., Toronto, Ontario (CA)

( * ) Notice: Subject to any disclaimer, the term of this patent is extended or adjusted under 35 U.S.C. 154(b) by 862 days.

(21) Appl. No.: 12/459,292

(22) Filed: Jun. 30, 2009

Related U.S. Application Data

(60) Provisional application No. 61/133,768, filed on Jul. 2, 2008.

(51) Int. Cl.
*B25J 18/06* (2006.01)
(52) U.S. Cl. .......................... 74/490.04; 606/1; 901/21
(58) Field of Classification Search .............. 74/490.04; 600/139, 140, 141, 142; 606/1; 901/21
See application file for complete search history.

(56) References Cited

U.S. PATENT DOCUMENTS

| | | | | |
|---|---|---|---|---|
| 5,297,443 A * | 3/1994 | Wentz | .......................... | 74/490.04 |
| 5,842,381 A * | 12/1998 | Feiten | .......................... | 74/490.04 |
| 6,485,411 B1 * | 11/2002 | Konstorum et al. | .......... | 600/139 |
| 6,602,187 B2 * | 8/2003 | Takase | .......................... | 600/140 |
| 7,579,550 B2 * | 8/2009 | Dayton et al. | ................. | 174/108 |
| 7,850,604 B2 * | 12/2010 | Wimmer | ........................ | 600/139 |
| 2004/0243108 A1 * | 12/2004 | Suzuki | .............................. | 606/1 |

* cited by examiner

*Primary Examiner* — William C Joyce
(74) *Attorney, Agent, or Firm* — Perry + Currier Inc.

(57) ABSTRACT

A system for navigating around healthy organs to reach a desired site of surgery is provided. The system includes an articulating shaft capable of navigating around healthy organs in a body. The articulating shaft includes a plurality of shaft sections and one or more movable joints. Further, the one or more movable joints have a two-degree of freedom motion. The two-degree of freedom joints operatively connect the plurality of shaft sections. Moreover, the system includes one or more cables which aid in controlling the movements of the movable joints. Additionally, the system can include a variety of medical tools located at the tip of a shaft section of the articulating shaft, wherein the medical tool aids in performing the medical activity.

4 Claims, 5 Drawing Sheets

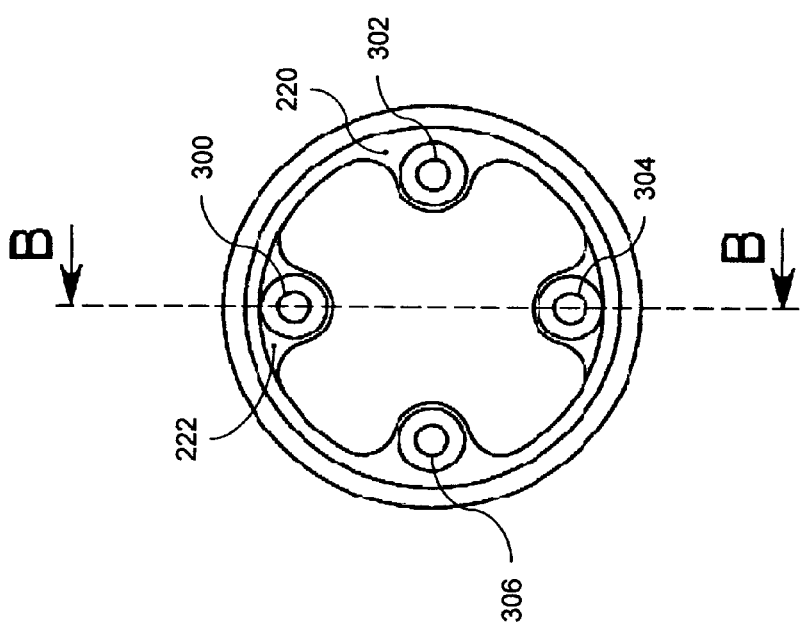
FIG. 3
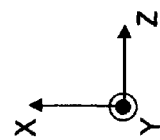

SECTION B-B

//MULTI ARTICULATING ROBATIC INSTRUMENT

CROSS REFERENCE TO RELATED APPLICATION

This application claims priority of U.S. Provisional Application No. 61/133,768 filed Jul. 2, 2008 which is incorporated by reference herein.

FIELD OF INVENTION

The invention disclosed here relates in general to the field of robotic systems, and more particularly, to a multi articulating robotic instrument for medical applications.

BACKGROUND

While performing a surgery, the normal practice is to make a single long incision on the patient's body where surgery is to be performed. Although this helps ease access to the site of surgery, the chances of infection also increase. Further, the recovery time of the patient is increased due to factors such as blood loss and extensive tissue damage. Further, at times, the surgeon may forget a foreign object in the patient's body, which could further lead to serious post-operative complications.

The next generation of surgery includes minimal invasive surgery (MIS) which is performed by making small incisions ranging from 1-3 cm, and using pencil-sized instruments for the surgery. The instruments are entered through the small incisions and passed through natural body cavities. Due to the small nature of incisions and minimum exposure of the interior portions of the body, healing is faster and chances of infection or of post-operative complications are less. Further, this surgical process leaves minimal scars on the skin surface. The pencil-sized instruments being used for MIS include robotic instruments which augment the process by increasing precision, articulation and manipulation and three-dimensional magnification of the site of surgery.

Most of the available robotic instruments used for MIS include a straight, elongated shaft which enters into the body of the patient through the small incisions. These shafts can carry imaging equipments such as a camera, as well as surgical instruments such as forceps and scissors. However, the straight, elongated shafts lack the capability of navigating around a healthy organ. If such a healthy organ is encountered between the entry site (port), i.e. the point of incision in the body wall, and the surgical site, the straight, elongated shafts cannot navigate around to reach the surgical site.

In light of the foregoing discussion, there is a need of a simple system and method for navigating around obstacles to reach the surgery site. While possessing navigational capabilities, the system should also be rigid enough to allow a surgeon to perform an operation at the surgery site in a steady manner. Moreover, the system should be capable of carrying a variety of instruments, such as forceps, scissors and needle drivers.

SUMMARY

It is an object of the present invention to provide a robotic instrument suitable for being used in medical activities. The robotic instrument comprises an articulating shaft, the articulating shaft including a plurality of shaft sections and one or more movable joints operatively coupling each of the plurality of shaft sections. The one or more movable joints further include a plurality of double helix sections, each of the plurality of double helix sections configured to move in one degree of freedom of motion. The one or more movable joints are thus configured to move the shaft sections with at least two degrees of freedom of motion. Each of the plurality of double helix sections further includes a plurality of bumper and socket arrangements for providing the necessary rigidity to the instrument. The robotic instrument further comprises at least one medical tool attached to a distal end of the articulating shaft.

BRIEF DESCRIPTION OF THE DRAWINGS

The preferred embodiments of the invention will hereinafter be described in conjunction with the appended drawings provided to illustrate and not to limit the invention, wherein like designations denote like elements, and in which:

FIG. 3 illustrates a top-view of the movable joint, in accordance with an embodiment of the present invention;

DETAILED DESCRIPTION OF THE INVENTION

While the preferred embodiments of the invention have been illustrated and described, it will be clear that the invention is not limited to these embodiments only. Numerous modifications, changes, variations, substitutions and equivalents will be apparent to those skilled in the art without departing from the spirit and scope of the invention.

The present invention provides a robotic instrument to be used during a medical activity such as a surgery or an endoscopy. The instrument possesses the capability of navigating around healthy organs in a body during the medical activity. For this purpose, the instrument includes an articulating shaft capable of providing the said navigation capability and a medical tool attached to the distal end of the shaft. A few examples of the medical tool include, but are not limited to, forceps, scissors, a needle driver, and an imaging device such as a camera.

Figure 1:
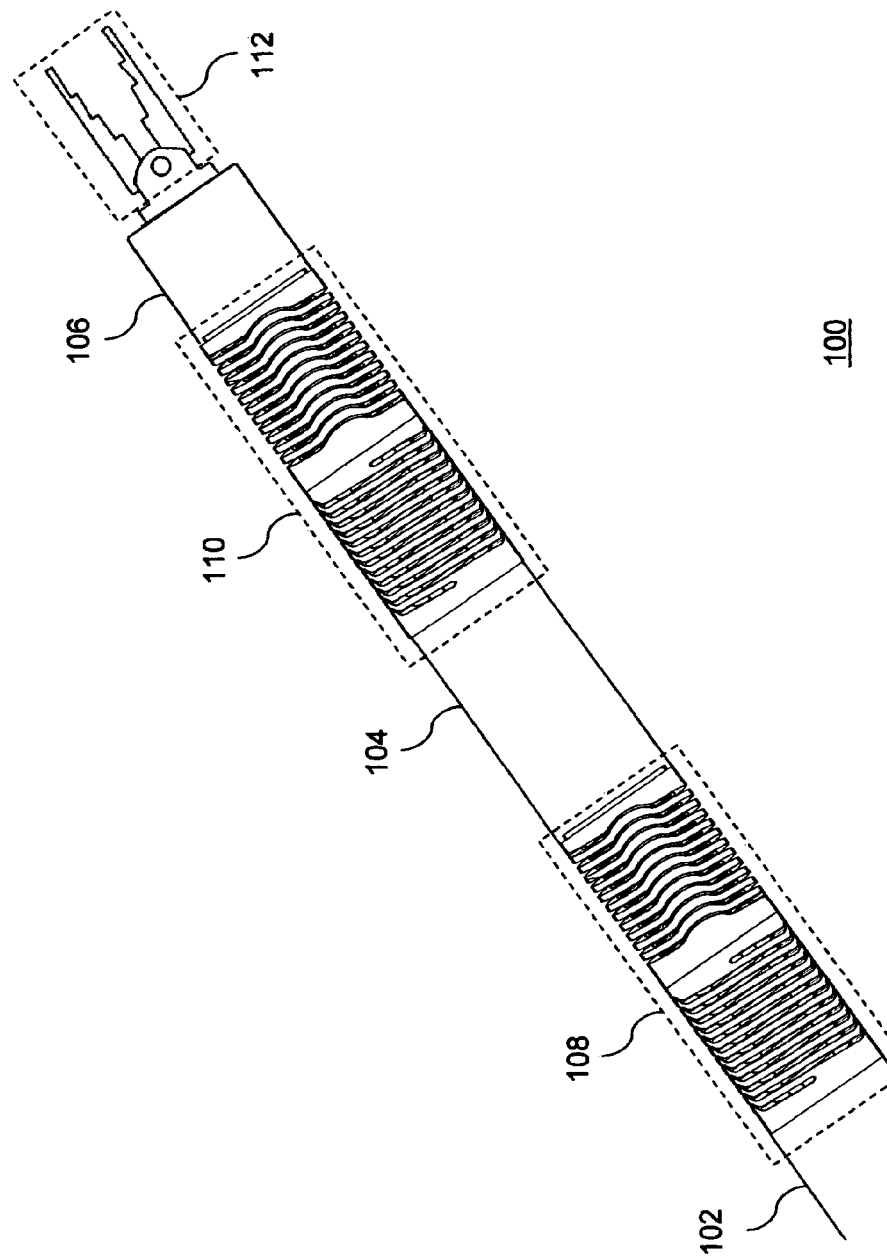
FIG. 1 illustrates a side-view of an articulating shaft, in accordance with an embodiment of the present invention.

FIG. 1 illustrates a side-view of an articulating shaft 100 of the robotic instrument, in accordance with an embodiment of the present invention. The articulating shaft 100 includes three shaft sections 102, 104, and 106, a pair of movable joints 108 and 110, and a medical tool 112 attached to its distal end. In another embodiment, the articulating shaft 100 can include any number of shaft sections, and any number of movable joints depending upon the complexity of movement required. In yet another embodiment, more than one medical tool can be attached to the articulating shaft 100.

Movable joint 108 operatively couples the shaft sections 102 and 104, while movable joint 110 operatively couples the shaft sections 104 and 106. Further, the movable joints 108 and 110 are configured to move the three shaft sections 102, 104, and 106 in at least two degree of freedom. The movable joint 110, closer to the medical tool 112, can be termed as a distal movable joint and the movable joint 108, farther from the medical tool 112, can be termed as a proximal movable joint. In various embodiments, the shaft sections 102, 104 and 106 can be made of materials such as 17-4PH stainless steel, a titanium alloy, a carbon fiber, a biocompatible material, nylon, plastic or combinations thereof. However, it should be evident to a person of ordinary skill in the art that the shaft sections can be manufactured from other materials.

The articulating shaft 100 also includes one or more cables (not shown in the figure) which aid in controlling the movement of the movable joints 108 and 110, and hence aid in navigation of the articulating shaft 100.

Figure 2:
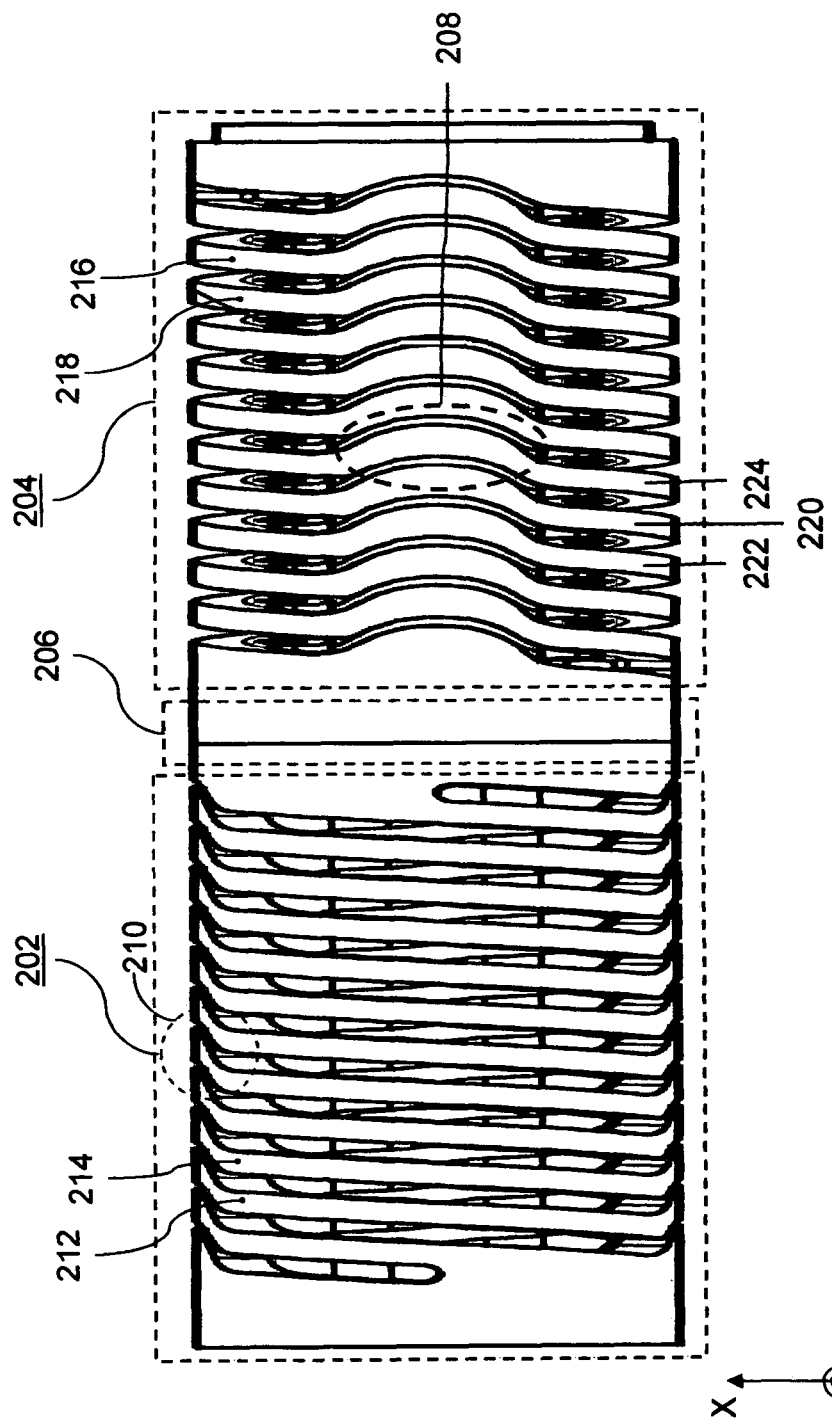
FIG. 2 illustrates a side-view of a movable joint, in accordance with an embodiment of the present invention.

FIG. 2 illustrates a side-view of the movable joint 108, in accordance with an embodiment of the present invention. The movable joint 108 is the proximal movable joint, and is shown to include two helix sections 202 and 204. In another embodiment, the movable joint 108 can include any number of helix sections.

The helix sections 202 and 204 are configured to move in one degree of freedom motion. Each of the helix sections 202 and 204 possesses a double-helix design. In another embodiment, the helix sections 202 and 204 can also possess a single helix structure. In yet another embodiment, helix sections 202 and 204 can be a single continuous element or made up of individual elements.

Within each of the helix sections 202 and 204, each helix is displaced by 90 degrees with respect to the adjacent helix. Hence, the movable joint 108 contains four helices 212, 214, 216 and 218. Also, the pair of helices 212 and 214 is separated from the pair of helices 216 and 218 by a spacer 206. The double-helix design helps in providing flexibility during actuation and navigation. Further, the double-helix design can also include arrangements to provide the required stiffness when the movable joint 108 bends to reach the surgery site and to use the medical tool 112. For example, bending motion of the helix section 204 is restricted in the Y-Z plane due to the presence of a bumper and socket arrangement 208 on the coil turn 224. This arrangement has been explained in detail in FIG. 5. This restriction on bending movement of the helix section 204 provides the required stiffness in the Y-Z plane.

Additionally, the helix section 202 is also shown to include a bumper and socket arrangement, 210, that is similar to the bumper and socket arrangement 208. The bumper and socket arrangement also aids in countering the compression effect produced due to bending the movable joint 108 along any of the helix sections 202 and 204. The four helices 212, 214, 216 and 218 are arranged in such a manner so as to allow each of the two helix sections 202 and 204 to bend in a plane normal to each other. For example, as shown in FIG. 1, first helix section 202 can bend in the Y-Z plane, whereas second helix section 204 can bend in the X-Y plane.

In various embodiments, the movable joint 108 can be composed of a wide variety of materials to vary the mechanical properties. Additionally, various parameters of the helices, such as radius, pitch, spacing and degree of offset can be varied to tailor the bending mechanics of the movable joint 108 to particular medical applications.

FIG. 3 illustrates a top-view of the movable joint 108, in accordance with an embodiment of the present invention. The helices of the movable joint 108 are shown to include one or more index holes 300, 302, 304 and 306. The index holes 300, 302, 304 and 306 are present on sections protruding from the inner curved surface of one or more coil turns of the helices 216 and 218, as shown in FIG. 3. In another embodiment, the positioning and number of the index holes can be different from the one mentioned above. Further, axes of the index holes are aligned along the Y-axis, as shown in FIGS. 2 and 3. The index holes 300, 302, 304 and 306 act as guides for one or more cables (not shown in the figure) that facilitate the movement of the movable joint 108.

Further, the four index holes 300, 302, 304 and 306 can be placed on the coil turns of the helices 216 and 218 in various possible arrangements based on the requirement to modify the bending mechanics of the movable joint 108 for various medical applications. In one embodiment, two of the four index holes, for example index holes 300 and 304 can be placed on a coil turn of the helix 218, and the other two index holes 302 and 306 can be placed on a coil turn of the helix 216. For example, as shown in FIGS. 2 and 3, the index holes 300 and 304 can be placed on the coil turn 222 of the helix 218. Further, the index holes 302 and 306 can be placed on the coil turn 220 of the helix 216. In an alternate embodiment, all the four index holes 300, 302, 304 and 306 can be placed on the same coil turn of a helix. For example, all the four index holes 300, 302, 304 and 306 can be placed on the coil turn 220 of the helix 216.

In various embodiments of the present invention, the one or more cables can be composed of bio-compatible materials, a stainless steel, a titanium alloy, a carbon fiber, nylon, plastic or combinations thereof. However, it should be evident to a person of ordinary skill in the art that the one or more cables can be manufactured from other materials. Furthermore, the strength and thickness of the one or more cables can also be varied depending on the force of actuation required to control the movable joint 108 during navigation. Also, in various embodiments, the number of cables required for navigation can vary depending upon the number of movable joints in the articulating shaft 100.

In an exemplary embodiment, a set of four actuating cables can pass through the four index holes 300, 302, 304 and 306 of the movable joint 108. Two cables of the set can terminate in the first helix section 202 of the movable joint 108, thereby providing a bending actuation force in the Y-Z plane for the first helix section 202. The remaining two cables can pass through the first helix section 202, and terminate in the second helix section 204 of the movable joint 108, thereby providing a bending actuation force in the X-Y plane for the second helix section 204. In a similar manner, another set of four cables can pass through the shaft section 102, the proximal movable joint 108 and shaft section 104, terminating at the distal movable joint 110. In various embodiments, the distance between the movable joints 108 and 110 can be varied to tailor the navigational capabilities of the articulating shaft to get around the healthy organs and reach a surgical target organ.

Figure 4:
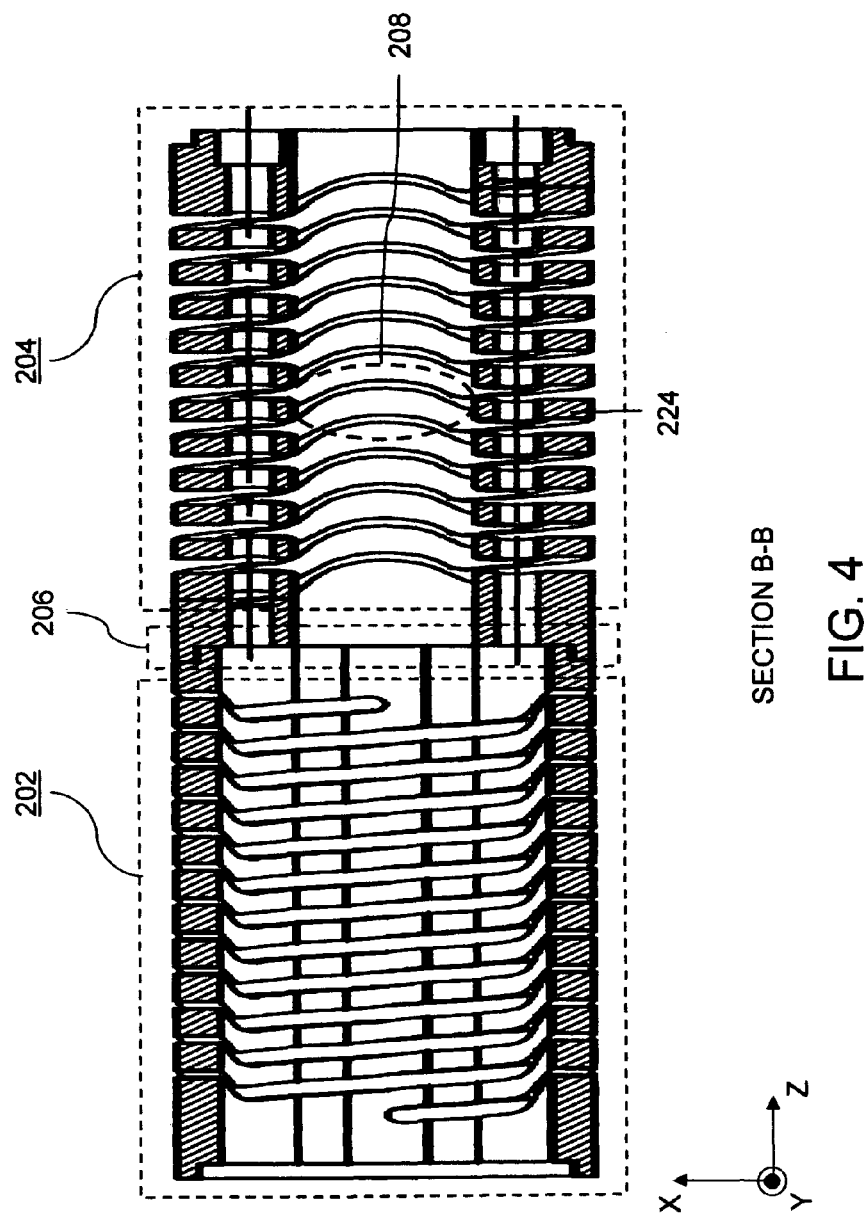
FIG. 4 illustrates a cross-sectional view of the movable joint taken along line B-B of FIG. 2, in accordance with an embodiment of the present invention.

FIG. 4 illustrates a cross-sectional view of the movable joint 108 taken along line B-B of FIG. 3, in accordance with an embodiment of the present invention. As shown in FIG. 4, each turn of the coils of the helices include a bumper and socket arrangement 208.

Figure 5:
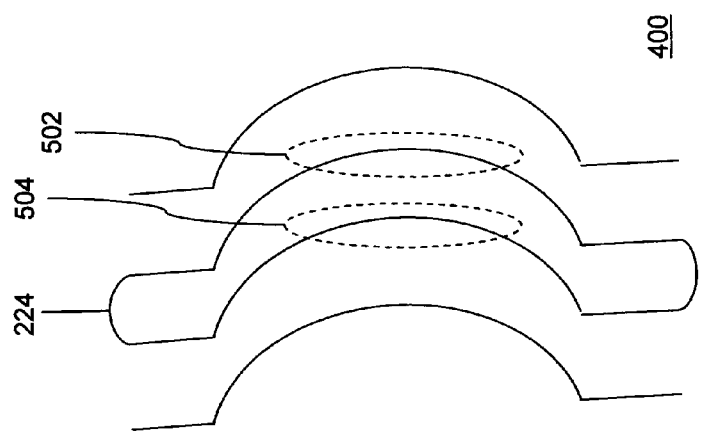
FIG. 5 illustrates a bumper and socket arrangement in the movable joint, in accordance with an embodiment of the present invention.

FIG. 5 illustrates the bumper and socket arrangement 208 on the coil turn 224 in the movable joint 108, in accordance with an embodiment of the present invention. The bumper and socket arrangement 208 is shown to include a bumper element 502 and a socket element 504, wherein the bumper element 502 protrudes outwards from the surface of the coil turn 224 and the socket element 504 protrudes inwards, forming a depression in the surface of the coil turn 224, as shown in FIG. 4. The bumper element 502 and the socket element 504 are machined onto the surface of the coil turn 224 as a single piece element. As a result, the bumper element 502 and socket element 504 are curved and coincident with the surface of the helix coils. In various embodiments, shape of the bumper element 502 and socket element 504 can be interlacing triangular teeth, rectangular type gears, or other interlacing shapes. However, it will be readily evident to a person of ordinary skill in the art that the bumper and socket elements can possess shapes that are different from those mentioned above. The bumper element 502 of the bumper and socket arrangement 208 can buttress against the socket element 504 of an adjacent bumper and socket arrangement when the helix section 204 is actuated. As a result, the bumper element 502 counters the compression effects generated due to contact of the outer surfaces of the bumper element 502 and the socket element 504. In an exemplary embodiment, the outer contact surfaces of the bumper element 502 and the socket element 504 can be smooth. In alternate embodiments, the outer contact surfaces can be roughened. The shape of the outer contact surfaces can also be varied. In one embodiment, the outer contact surfaces can be shaped in a sinusoidal wave mesh. In another embodiment, the outer contact surfaces can be shaped in a square wave mesh.

The movable joint 110 is similar in construction and functions to the movable joint 108 and includes components and functionalities as described in the figures above.

Various embodiments of the present invention offer one or more advantages. The present invention provides an instrument for navigating around healthy organs to reach the surgery site. The relative movement between the movable joints allows at least two degrees of freedom movement for the articulating shaft carrying a variety of medical tools. Thus, the invention eliminates the need of bulky and space consuming mechanisms required to navigate the articulating shaft. Further, the invention enhances navigational capabilities of the articulating shaft and hence allows for easier navigation around the healthy organs to reach the target organ for surgery. Furthermore, the system is rigid enough, due to the bumper and socket arrangement, to perform the surgery in a steady manner.

What is claimed is:

1. A robotic instrument suitable for being used in medical activities, the robotic instrument comprising:
    an articulating shaft, the articulating shaft including a plurality of shaft sections, and one or more movable joints operatively coupling the plurality of shaft sections, the one or more movable joints including:
        a plurality of double helix sections, configured to move in one degree of freedom of motion, the one or more movable joints configured to move the shaft sections with at least two degrees of freedom of motion, the plurality of double helix sections further including a plurality of bumper and socket arrangements, wherein a helix of the plurality of double helix sections comprises one or more holes, the one or more holes acting as a guide for one or more cables, the one or more cobles facilitating movement of the one or more movable joints; and
    at least one medical tool, the at least one medical tool attached to a distal end of the articulating shaft.

2. The robotic instrument according to claim 1, wherein the one or more holes are located at one or more coil turns of a helix of the plurality of double helix sections.

3. The robotic instrument according to claim 1, wherein the one or more movable joints are made of at least one of a 17-4PH stainless steel, a titanium alloy, a carbon fiber, a biocompatible material, a biocompatible nylon, and a plastic.

4. The robotic instrument according to claim 1, wherein the medical tool is at least one of forceps, scissors, a needle driver, and an imaging device.

\* \* \* \* \*